(12) United States Patent
Terahara et al.

(10) Patent No.: US 8,747,362 B2
(45) Date of Patent: Jun. 10, 2014

(54) MICRONEEDLE DEVICE

(75) Inventors: Takaaki Terahara, Tsukuba (JP); Seiji Tokumoto, Tsukuba (JP)

(73) Assignee: Hisamitsu Pharmaceutical Co., Inc, Tosu-Shi, Saga (JP)

( * ) Notice: Subject to any disclaimer, the term of this patent is extended or adjusted under 35 U.S.C. 154(b) by 43 days.

(21) Appl. No.: 13/376,656

(22) PCT Filed: Jun. 10, 2010

(86) PCT No.: PCT/JP2010/059848
§ 371 (c)(1),
(2), (4) Date: Feb. 10, 2012

(87) PCT Pub. No.: WO2010/143689
PCT Pub. Date: Dec. 16, 2010

(65) Prior Publication Data
US 2012/0130306 A1  May 24, 2012

(30) Foreign Application Priority Data
Jun. 10, 2009 (JP) ................ P2009-139582

(51) Int. Cl.
*A61M 5/00* (2006.01)
*A61N 1/30* (2006.01)

(52) U.S. Cl.
USPC ........................................... 604/173; 604/21

(58) Field of Classification Search
USPC .................................. 604/21, 173
See application file for complete search history.

(56) References Cited

U.S. PATENT DOCUMENTS

| 6,611,707 B1 * | 8/2003 | Prausnitz et al. ............... 604/21 |
| 7,527,802 B2 * | 5/2009 | Glenn et al. ................ 424/257.1 |
| 7,914,813 B2 * | 3/2011 | Adachi et al. ................. 424/449 |
| 2004/0049150 A1 | 3/2004 | Dalton et al. |

(Continued)

FOREIGN PATENT DOCUMENTS

| CN | 1511590 A | 7/2004 |
| EP | 1 632 263 A1 | 3/2006 |

(Continued)

OTHER PUBLICATIONS

Office Action for Chinese Patent Application No. 201080025513.8; issued Nov. 14, 2012.

(Continued)

*Primary Examiner* — Nicholas Lucchesi
*Assistant Examiner* — Weng Lee
(74) *Attorney, Agent, or Firm* — Nath, Goldberg & Meyer (57) ABSTRACT

Provided is a microneedle device where a coating agent has been applied to microneedles having a biodegradable resin. It has been found that the application of the coating agent to microneedles of a biodegradable resin having a predetermined strength allows the microneedles to have excellent performance. Further, with regard to the coating agent, a predetermined type and amount thereof are also useful to demonstrate performance. Accordingly, when a microneedle device 1 is arranged so that at least a part of a microneedle array 2 provided with microneedles 3 made from polylactic acid having a weight average molecular weight of 40,000 or more is coated with a carrier containing physiologically active ingredients, it is possible to attain excellent migration characteristics of the physiologically active ingredients to a living body.

7 Claims, 6 Drawing Sheets

(56) References Cited

U.S. PATENT DOCUMENTS

| | | |
|---|---|---|
| 2004/0120848 A1 | 6/2004 | Teodorczyk |
| 2006/0127465 A1* | 6/2006 | Maenosono et al. .......... 424/449 |
| 2008/0051699 A1* | 2/2008 | Choi et al. ..................... 604/46 |
| 2008/0208134 A1 | 8/2008 | Tomono |
| 2008/0312610 A1 | 12/2008 | Binks et al. |
| 2009/0030365 A1 | 1/2009 | Tokumoto et al. |
| 2009/0099502 A1 | 4/2009 | Tokumoto et al. |
| 2009/0292254 A1 | 11/2009 | Tomono |
| 2009/0292255 A1 | 11/2009 | Tomono |
| 2010/0030100 A1 | 2/2010 | Tokumoto et al. |
| 2010/0221314 A1 | 9/2010 | Matsudo et al. |
| 2010/0280457 A1 | 11/2010 | Tokumoto et al. |

FOREIGN PATENT DOCUMENTS

| | | |
|---|---|---|
| EP | 2 457 592 A1 | 5/2012 |
| JP | 11-286439 A | 10/1999 |
| JP | 2005-21677 A | 1/2005 |
| JP | 2006-341089 A | 12/2006 |
| JP | 2007-37626 A | 2/2007 |
| JP | 2008-212588 A | 9/2008 |
| JP | 2009-502261 A | 1/2009 |
| JP | 2009-72271 A | 4/2009 |
| WO | 98/28037 A1 | 7/1998 |
| WO | 2005/044366 A2 | 5/2005 |
| WO | 2005/069758 A2 | 8/2005 |
| WO | 2006/121110 A1 | 11/2006 |
| WO | 2008/096732 A1 | 8/2008 |
| WO | 2008/139648 A1 | 11/2008 |
| WO | 2009/001671 A1 | 12/2008 |
| WO | 2009/051147 A1 | 4/2009 |
| WO | 2010/013601 A1 | 2/2010 |
| WO | 2010/074239 A1 | 7/2010 |
| WO | 2010/087300 A1 | 8/2010 |
| WO | 2011/05508 A1 | 9/2011 |

OTHER PUBLICATIONS

The International Search Report for International PCT Application No. PCT/JP2010/059848; mailed Jul. 6, 2010; two pages.
International Preliminary Report on Patentability for PCT Application No. PCT/JP2010/059848; 6 pages; mailed on Jan. 26, 2012.
Harvinder S. Gill, et al., "Coating Formulations for Microneedles", Pharmaceutical Research, vol. 24, No. 7, Jul. 2007, pp. 1369-1380.
Chisato Yoshimura, et al., "Polylactic Acid-sei Microneedle Array no Kino Hyoka", Abstract of Annual Meeting of Pharmaceutical Society of Japan, No. 124th, No. 4, III-173, 2004, p. 68. English translation attached separately.
EPO Search Report, issued on Apr. 4, 2013, in counterpart EP Patent Application No. 10786220.3, seven (7) pages.
Office Action issued in Chinese Patent Application No. 201080025513.8 dated Jan. 27, 2014, 8 pages.

* cited by examiner

MICRONEEDLE DEVICE

This is a National Phase Application filed under 35 U.S.C. §371 as a national stage of PCT/JP2010/0059848, filed on Jun. 10, 2010, an application claiming the benefit under 35 U.S.C. §119 of Japanese Application No. P2009-139582, filed on Jun. 10, 2009, the content of each of which is hereby incorporated by reference in their entirety.

TECHNICAL FIELD

The present invention relates to a microneedle device including a microneedle array provided with one or more microneedles capable of piercing skin on a base for administration of drugs to a living body, sucking extraction of blood from a living body, or the like.

BACKGROUND ART

Conventionally, a microneedle device has been known as a device for improving transdermal absorption of drugs. A microneedle device includes a microneedle array, and microneedles provided on a base of the microneedle array are intended to pierce the stratum corneum, which is an outermost skin layer, and various sizes and shapes thereof have been proposed. A microneedle device is expected as a non-invasive administration method (for example, see Patent Literature 1).

Further, various methods have also been proposed in regard to a method of applying drugs by use of a microneedle array. Coating the surface of microneedles with drugs, forming a groove or a hollow part in microneedles through which drugs or body components are allowed to penetrate, mixing drugs into microneedles themselves, and the like are known (Patent Literature 2).

Patent Literature 3 states that in a drug transdermal pad base, in a case where fine needles provided on a skin-side surface thereof are made from a biodegradable resin, even if a tip of a fine needle is chipped and remains in skin, the fine needle made from the biodegradable resin is degraded within a living body, thereby causing little adverse effect on the living body, and that as the biodegradable resin, polylactic acid, polyethylene succinate, polybutylene succinate adipate, polybutylene succinate carbonate, polycaprolactone, polyester amide, polyester carbonate, polyvinyl alcohol, polyhydroxy butylate, maltotriose, cellulose, cellulose acetate, collagen, and mixtures thereof are recommended, and polylactic acid or a copolymer of lactic acid and glycolic acid is particularly preferable.

Further, Patent Literature 3 states that in the case of polylactic acid, when its weight average molecular weight is 100,000 to 500,000, an amount thereof deposited to the aforementioned metal thin wire is suitable in view of production, a pulling-out property of the metal thin wire after hardening of the resin is good, and the quality of a finished film (a tubular object) is also excellent. However, Patent Literature 3 does not describe anything about molecular weight and strength.

Patent Literature 4 discloses that in a drug release system which can select and perform any of controlled biphasic release, sustained release, and delayed release, pulverized polylactic acid having a weight average molecular weight of 3000 to 40,000 is used, but it does not describe anything about a microneedle capable of piercing skin at all.

CITATION LIST

Patent Literature

Patent Literature 1: National Publication of International Patent Application No. 2001-506904

Patent Literature 2: National Publication of International Patent Application No. 2004-504120

Patent Literature 3: Japanese Patent Application Laid-Open No. 2005-021678

Patent Literature 4: Japanese Patent Application Laid-Open No. 11-286439

SUMMARY OF INVENTION

Technical Problem

When a microneedle array is produced from a biodegradable resin, a step of deforming the biodegradable resin into a desired shape by heating it to be softened, and a sterilization operation or the like by an electron-beam irradiation treatment, etc are required. However, this causes a problem: the strength of the microneedle array (especially, a microneedle portion) decreases during such steps, thereby resulting in that the microneedles which are essentially supposed to pierce skin cannot perform its function, or the base of the microneedle array is broken at the time of use and cannot perform its function.

Further, another problem is that when a physiologically active ingredient is administered by use of such a microneedle array as a microneedle device, the efficiency of the administration is poor.

In view of this, it is an object of the present invention to provide a microneedle device in which a functional performance is efficiently maintained in a microneedle device.

Solution to Problem

To achieve the object, a coating agent has been applied to microneedles made from a biodegradable resin, and a relation between strength and performance thereof has been clarified. As a result thereof, it has been found that application of the coating agent to microneedles made from a biodegradable resin having a predetermined strength or more, that is, a predetermined weight average molecular weight or more, allows the microneedles to have excellent performance. Further, it has been found that in regard to the coating agent, a predetermined type and amount thereof are also useful to demonstrate the performance.

That is, a microneedle device according to the present invention includes a microneedle array provided with microneedles made from polylactic acid having a weight average molecular weight of 40,000 or more, wherein at least a part of the microneedle array is coated with a carrier containing physiologically active ingredients. According to this configuration, it is possible to attain excellent migration characteristics of the physiologically active ingredients to a living body, Note that the microneedle array according to the present invention indicates a configuration including at least microneedles. On the other hand, the microneedle device indicates a member which further includes other constituents in addition to the microneedle array, and it is distinguished from a configuration which only includes the microneedle array.

Further, in this microneedle device, it is preferable that the carrier is pullulan, propylene glycol, glycerin, or a carboxyvinyl polymer.

Advantageous Effects of Invention

According to the microneedle device of the present invention, by partially coating microneedles having a predetermined strength or more, with a carrier containing physiologically active ingredients (a coating agent), it is possible to attain excellent migration characteristics of the physiologically active ingredients to a living body.

DESCRIPTION OF EMBODIMENTS

Hereinbelow, a microneedle device including a microneedle array according to one embodiment of the present invention will be described with reference to drawings.

Figure 1:
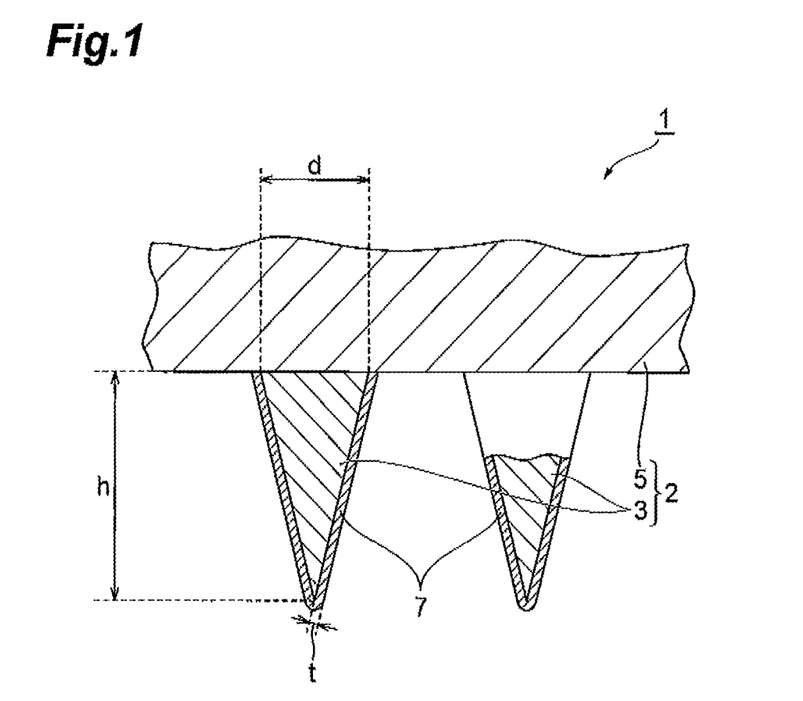
FIG. 1 is an enlarged cross-sectional view schematically showing a microneedle device according to the present invention.

As shown in FIG. 1, a microneedle device 1 includes a microneedle array 2. The microneedle array 2 is constituted by microneedles (needles) 3 for piercing skin or a mucous membrane and a microneedle base 5 which supports them, and thus, a plurality of microneedles 3 are arrayed on the microneedle base 5. The microneedle 3 has a minute structure, and a height (length) h of the microneedle 3 is preferably 50 µm to 700 µm. Here, the reason why the length h of the microneedle 3 is set to 50 µm or more is to surely perform transdermal administration of physiologically active ingredients and the reason why the length h thereof is set to 700 µm or less is to avoid the contact of a nervous system with the microneedle 3, thereby making it surely possible to reduce possibilities of pain, and to surely avoid possibilities of bleeding at the same time. Further, when the length h is 700 µm or less, it is possible to efficiently administer an amount of physiologically active ingredients penetrating the skin.

At this point, the microneedle 3 refers to a projecting structure including, in a broad sense, a needle shape or a structure containing a needle shape, and when the microneedle 3 has a conical-shaped structure, a diameter d of a basal surface thereof is generally about 50 to 200 µm. Further, the microneedle 3 is not limited to a structure having a needle shape, in a narrow sense, with a tapered tip but also includes a structure without a tapered tip, microscopically. In consideration of cases where the microneedle 3 is broken on skin, the microneedle 3 is produced from polylactic acid, which is a biodegradable resin. In some cases, physiologically active ingredients may be mixed in the resin so that the physiologically active ingredients can be released in a body at the same time as the microneedle 3 is dissolved in the body.

Note that, examples of the polylactic acid include polylactic acid homopolymers such as polyL-lactic acid and polyplactic acid, a polyL/D-lactic acid copolymer, and a mixture thereof, but any of these may be used. Further, additives such as a plasticizer, an anti-blocking agent, a lubricant, an antistatic agent, and a heat stabilizer can be added to the polylactic acid as appropriate.

The polylactic acid resin tends to have higher strength as its weight average molecular weight is larger. For example, although the weight average molecular weight decreases to around 65 to 99% of an original weight average molecular weight thereof due to electron-beam irradiation, in order to keep the strength even after the electron-beam irradiation, it is necessary for the polylactic acid resin to have a weight average molecular weight of 40,000 or more. Thus, before the electron-beam irradiation, it is necessary for the polylactic acid resin to have a weight average molecular weight of at least 40,000 or more.

More preferably, it is necessary for the polylactic acid resin to have a weight average molecular weight of 50,000 or more in terms of strength. In view of this, before the electron-beam irradiation, it is necessary for the weight average molecular weight to be at least 50,000 or more.

If the weight average molecular weight after the electron-beam irradiation is 40,000 or more, the microneedle 3 can be used without losing its performance, but preferably, it is necessary for the weight average molecular weight after the electron-beam irradiation to be 50,000 or more.

The upper limit of the weight average molecular weight of the polylactic acid resin is not set in particular, but when the weight average molecular weight after the electron-beam irradiation exceeds 500,000, for example, the following problem may occur: processing of the microneedle 3 is difficult.

A sterilization process can be performed by a well-known method that is generally performed, but it is preferable for sterilization of the microneedle array 2 to be performed by electron-beam irradiation or gamma-ray irradiation. Measurement of an electron-beam irradiation dose is performed on the top or bottom of an irradiation sample, or on a supporting material (e.g., a "cardboard"), and thus it is possible to check that the sample is irradiated with a predetermined irradiation dose (under an irradiation environment with a temperature of 15° C. and a humidity of 15%). On the other hand, in the case of the gamma-ray irradiation, an irradiation sample can be irradiated with cobalt-60 gamma rays according to a designated irradiation dose of 5 to 100 kGy.

The microneedle base 5 is a foundation to support the microneedles 3. A configuration thereof is not limited, and may be, for example, a base having holes penetrating therethrough, which allows for administration of physiologically active ingredients from the back of the base. Examples of a material of the microneedles 3 or the microneedle base 5 include silicon, silicon dioxide, ceramics, metals (such as stainless steel, titanium, nickel, molybdenum, chromium, and cobalt), and synthetic or natural resin materials, but in consideration of the antigenicity of the microneedles 3 and the unit price of the material, biodegradable polymers such as polylactic acid, polyglycolide, polylactic acid-co-polyglycolide, pullulan, capronolactone, polyurethane, and polyanhydride, and synthetic or natural resin materials such as polycarbonate, polymethacrylic acid, ethylenevinyl acetate, polytetrafluoroethylene, and polyoxymethylene, which are non-biodegradable polymers, are particularly preferable. Further, the base may be integrated with the microneedles 3 in some cases, and, in those cases, the base is made from the same material as the aforementioned resin material of the microneedles 3.

The area of the microneedle base 5 is 0.5 $cm^2$ to 10 $cm^2$, preferably 1 $cm^2$ to 5 $cm^2$, and more preferably 1 $cm^2$ to 3 $cm^2$. Note that several microneedle bases 5 can be connected in combination to have a more favorite size.

As to the density of the microneedles (needles) 3, rows of the microneedles 3 are typically spaced apart so that a density of approximately 1 to 10 needles per millimeter (mm) is provided. Generally, adjacent rows are spaced apart from each other by a distance substantially equal to the space between the needles in a row, and the needle density is 100 to 10000 needles per 1 $cm^2$. When there is a needle density of 100 needles or more, the needles can efficiently pierce skin. Meanwhile, a needle density of more than 10000 needles makes it difficult to give the microneedles 3 strength capable of piercing skin. The density of the microneedles (needles) 3 is preferably 200 to 5000 needles, more preferably 300 to 2000 needles per 1 $cm^2$.

Examples of a production method of the microneedle array 2 include a wet etching process or a dry etching process using a silicon base, precision machining using metals or resins (such as an electric discharge method, laser processing, dicing processing, a hot embossing process, and injection mold processing), and machinery cutting. By these processing methods, a needle part and a support part are molded into an integrated unit. Examples of a method for hollowing the needle part include a method in which, following the production of the needle part, secondary processing such as laser processing is performed.

Note that a product obtained by coating the microneedle array 2 with the after-mentioned coating 7 is the microneedle device 1. Further, the present embodiment exemplifies a form in which the microneedles 3, which are a part of the microneedle array 2, are coated with the coating 7, but both the microneedles 3 and the microneedle base 5 may be coated with the coating 7.

As a storage method of the microneedle device 1, in consideration of a decrease in the weight average molecular weight due to long-term storage and a decrease in strength along with that, it is preferable to store the microneedle device 1 at a relative humidity of 20% or less. More preferably, the humidity is 10% or less, further more preferably the humidity is 3% or less.

Here, when the largest amount of water vapor ($kg \cdot m^{-3}$: saturated humidity) which the air in a given volume at 25° C. can have is assumed 100, the relative humidity refers to a percentage (%) of the amount of water vapor ($kg \cdot m^{-3}$) actually included in the air, relative to the largest amount of water vapor.

In order to maintain the relative humidity, it is preferable that the microneedle device 1 according to the present embodiment be stored in a container or a bag together with a drying agent enclosed therein. As the drying agent, ones made from well-known materials and generally used as the drying agent are applicable, and examples thereof include a drying agent made from a substance having a capability of physically or chemically adsorbing moisture. Especially, a physical drying agent capable of physically adsorbing moisture is preferable because it is easy to handle, it rarely contaminates the microneedle device 1, and its drying capability is high.

As the physical drying agent, a powdery substance made from a porous substance is preferable. More specifically, examples of the porous substance include a porous substance made from a metal oxide which is an amorphous porous substance, a porous substance made from zeolite which is a crystalline porous substance, or a porous substance made from a clay mineral which is a crystalline or noncrystalline porous substance. More specifically, examples of the metal-oxide porous substance include silicagel and alumina, examples of the zeolite porous substance include molecular sieves, and examples of the clay-mineral porous substance include montmorillonite.

Among them, it is preferable that the substance constituting the drying agent be silicagel, a molecular sieve, or montmorillonite. Note that these may be used solely, or two or more of them may be used in combination. When the above porous substances are used as the drying agent, the size and the like of fine pores thereof are not limited in particular, and any porous substance having mesopores, micropores or the like can be selected appropriately to use.

When coating is performed on the microneedles 3, in order to minimize changes in drug concentrations and physical properties caused by volatilization of a solvent of a coating agent, it is preferable to control temperature and humidity in an installation environment of an apparatus at a constant level. In order to prevent solvent evaporation, it is preferable to either decrease the temperature or increase the humidity, or control both. The humidity at room temperature when the temperature is not controlled is, as a relative humidity, 50 to 100% RH, preferably 70.0 to 100% RH, and most preferably 90 to 100% RH. When the humidity is 50% RH or less, significant solvent evaporation occurs, thereby causing physical properties of a coating solution to change. Although a humidification method is not limited to any particular method as long as an intended humidity condition can be assured, examples thereof include a gas system, a steam vapor system, and a water spray system. As a thickening agent mixed into the coating agent, it is preferable to select a water-soluble polymer which has high wettability and moisture retaining properties that restrain the volatility of the solvent as much as possible.

Further, the coating agent can contain physiologically active ingredients in purified water and/or a coating carrier, whereby the microneedle 3 can be coated with the coating agent, and examples of the coating carrier include polyethylene oxide, hydroxy methylcellulose, hydroxypropyl cellulose, hydroxypropyl methylcellulose, methylcellulose, carboxymethylcellulose, dextran, polyethylene glycol, polyvinyl alcohol, polyvinyl pyrrolidone, pullulan, carmellose sodium, chondroitin sulfate, hyaluronic acid, sodium hyaluronate, dextrin, gum arabic, ethanol, isopropanol, methanol, propanol, butanol, propylene glycol, dimethyl sulfoxide, glycerin, N,N-dimethylformamide, polyethylene glycol, benzyl benzoate, sesame oil, soybean oil, lactic acid, benzyl alcohol, polysorbate 80, alpha thioglycerin, ethylenediamine, N,N-dimethylacetamide, thioglycolic acid, and phenoxy ethanol. Among them, for the microneedles 3 having a predetermined strength, pullulan, propylene glycol, glycerin, and a carboxyvinyl polymer are preferable from the viewpoint of migration characteristics of physiologically active ingredients, and the like.

A content of the coating carrier in the coating agent is 0.1 to 70% by weight, preferably 1 to 60% by weight, and particularly preferably 1 to 30% by weight. The coating carrier may have to have a certain degree of viscosity so as not to drip, and a viscosity of approximately 100 to 100000 cps is necessary. A more preferable viscosity is 500 to 60000 cps. For the viscosity being within the above range, it is possible to apply a desired amount of the coating agent at once without depending on the material of the microneedles. Also, generally, there is a tendency that the higher the viscosity, the larger the amount of the coating agent.

A thickness t of the coating 7 of the microneedles 3 is less than 50 μm, preferably less than 25 μm, and more preferably 1 to 10 μm, Generally, the thickness t of the coating 7 is an average thickness as measured over the surface of the microneedles 3 after drying. The thickness t of the coating 7 can generally be increased by applying multiple films of the coating carrier, namely, by repeating a coating process after fixation of the coating carrier.

A content of the coating agent to be applied to each one of the microneedles 3 is not especially limited, but is preferably 10 to 300 μg, and more preferably 20 to 250 μg. When the content is 10 μg or less, it is difficult for the coating agent to contain a sufficient amount of physiologically active ingredients, but in the meantime, even if 300 μg or more of the coating agent is applied, piercing is not sufficiently performed, thereby resulting in that physiologically active ingredients cannot be administered, which tends to cause a loss of the physiologically active ingredients.

As has been already described above, the height (length) h of the microneedle 3 is preferably 50 μm to 700 μm. Although the height H of the coating of the microneedle 3 varies depending on the height h of the microneedle 3, it may be set in a range of 1 μm to 700 μm, usually within a range of 10 μm to 500 μm, preferably about 30 μm to 300 μm, and more preferably 100 μm to 200 μm. The height H of the coating in, this range tends to allow for more efficiently performing transdermal administration of the physiologically active ingredients contained in the coating when the microneedle 3 pierces skin, in combination with the hardness of the microneedle 3, that is, the material of the microneedle 3, the shape of the microneedle, and the piercing strength thereof. In addition, it is preferable the coating agent applied for coating be fixed by drying after the application.

A liquid composition used for coating the microneedles 3 is prepared by mixing biocompatible carriers, beneficial physiologically active ingredients to be delivered, and in some cases, any of coating aids with a volatile liquid. The volatile liquid can be water, dimethyl sulfoxide, dimethyl formamide, ethanol, isopropyl alcohol, a mixture thereof, and the like. Among them, water is most preferable. A coating agent in a liquid state or a suspension can typically have a concentration of the beneficial physiologically active ingredients of 0.1 to 65% by weight, preferably 1 to 30% by weight, more preferably 3 to 20% by weight. The coating is particularly preferably in a fixed state.

Other known pharmaceutical aids may be added to the coating as long as they do not adversely affect necessary solubility and characteristics of the viscosity of the coating as well as nature and physical properties of the dried coating.

As the physiologically active ingredient (drug) used in the present embodiment, peptide, protein, DNA, RNA, and the like are considered, but no particular limitation is imposed. Examples thereof include α-interferon, β-interferon for multiple sclerosis, erythropoietin, follitropin β, follitropin α, G-CSF, GM-CSF, human chorionic gonadotropin, luteinizing (leutinizing) hormone, salmon calcitonin, glucagon, GNRH antagonist, insulin, human growth hormone, filgrastim, heparin, low molecular weight heparin, and somatropin. Also, examples of a vaccine include Japanese encephalitis vaccine, rotavirus vaccine, Alzheimer's disease vaccine, arteriosclerosis vaccine, cancer vaccine, nicotine vaccine, diphtheria vaccine, tetanus vaccine, pertussis vaccine, Lyme disease vaccine, rabies vaccine, diplococcus pneumoniae vaccine, yellow fever vaccine, cholera vaccine, vaccinia vaccine, tuberculosis vaccine, rubella vaccine, measles vaccine, mumps vaccine, botulism vaccine, herpes vaccine, other DNA vaccines, and hepatitis B vaccine.

An administration method of the microneedle device 1 is not limited in particular, and a device for administration and a supplemental device to fix the microneedle device 1 may be used.

Further, administration time according to the method is not so long, and it is from several seconds to several minutes at longest, and depending on the case, instant administration, that takes less than a second is also possible. However, it is also possible to fix the microneedle device 1 on the skin thereafter for continuous administration of active ingredients.

Note that when a supplemental device is used, it is preferable that a collision energy of 0.05 to 0.7 J/cm$^2$ is applied to the microneedle device 1 from the supplemental device. On the other hand, when the microneedle device 1 is pushed, a force of 1.0 to 10 kg is applied to the device 1, and preferably a force of 1.0 to 7 kg, further preferably a force of 1.0 to 4 kg is applied to the device 1. Pushing time is not so long, and it is from several seconds to several minutes at longest, and depending on the case, instant administration that takes less than a second is also possible. The pushing time is preferably less than five minutes, and further preferably less than three minutes. Note that, instead of the pushing by hand, the physiologically active ingredients may be administered while a predetermined load is applied to the device 1 by fixing the microneedle device 1 to the skin. The microneedles 3 having a predetermined strength according to the present embodiment are never damaged even if such collision energy is applied to the microneedle device 1, thereby resulting in that physiologically active ingredients can be efficiently administered in a living body, which attains excellent migration characteristics of the physiologically active ingredients to the living body.

It is to be noted that these physiologically active ingredients (drugs) may be used solely or two or more thereof may be used in combination. Naturally, any drugs in a form of either an inorganic salt or an organic salt are encompassed as long as the salt is pharmaceutically acceptable. Further, while the drug is basically contained in the coating carrier, it is also possible to prepare a coating carrier without containing the drug, and separately supply the drug afterward via through holes (openings) formed in the microneedle base 5.

EXAMPLES

Example 1

In Example 1, an experiment was carried out in which samples of respective poly-L-lactic acid resins (weight average molecular weight: about 15,000 to 140,000) having different weight average molecular weights were irradiated with an electron beam and decreases in the weight average molecular weights of the polylactic acids due to the irradiation of the electron beam were measured. Note that an initial weight average molecular weight of a first sample (sample 1) which is a microneedle device made by Durect corporation is about 130,000. Further, an initial weight average molecular weight of a second sample (sample 2) is about 90,000. Furthermore, an initial weight average molecular weight of a third sample (sample 3) is about 130,000.

In this experiment, the weight average molecular weight of a poly-L-lactic acid resin was measured after microneedles were molded and irradiated with an electron beam of 40 kGy. The measurement of the weight average molecular weight was performed before molding (into a pellet form), after molding of microneedles, and after electron-beam irradiation, and the weight average molecular weight at each stage was measured by a gel filtration chromatography method (hereinafter, referred to as a GPC method). Note that, a weight average molecular weight (Mw/average) at an irradiation dose of "0 kGy," shown in Table 1, indicates a weight average molecular weight measured after a microneedle-molding step but before electron-beam irradiation (during the microneedle-molding step), and a decreasing rate at an irradiation dose of "0 kGy" indicates a decreasing rate during the microneedle-forming step. Further, a weight average molecular weight (Mw/average) at an irradiation dose of "40 kGy," shown in Table 1, indicates a weight average molecular weight measured after electron-beam irradiation of 40 kGy, and a decreasing rate at an irradiation dose of "40 kGy" indicates how much the weight average molecular weight decreases by electron-beam irradiation where a weight average molecular weight before electron-beam irradiation is "100" as a reference.

Further, as the sterilization method, both an electron-beam sterilization method and a gamma-ray sterilization method were used for comparison, among radiation sterilization methods (see Table 2). Note that Table 2 shows an experimental result on the sample 1.

As apparent in Table 1 and Table 2, such a tendency was shown that in the step (heating and cooling) of molding pellet-shape bulk powder into microneedles, the weight average molecular weight decreased to about 60% to 90% of the weight average molecular weight before the molding, and then, the weight average molecular weight further decreased depending on the irradiation dose by performing radiation sterilization. Moreover, in regard to the electron-beam sterilization method and the gamma-ray sterilization method, when they were compared at the same irradiation dose, such a tendency was shown that the electron-beam irradiation method had a lower decreasing rate of the weight average molecular weight. Measurement conditions and method of the weight average molecular weight are as follows.

Note that the measurement of an electron-beam irradiation dose was performed on the top or bottom of an irradiation sample, or on a supporting material (e.g., a "cardboard"), so as to check that the sample was irradiated with a predetermined irradiation dose (under an irradiation environment with a temperature of 15° C. and a humidity of 15%). On the other hand, in the case of the gamma-ray irradiation, an irradiation sample was irradiated with cobalt-60 gamma rays according to a designated irradiation dose of 5 to 100 kGy, and it was checked by an actual value that it was irradiated at a designated irradiation dose.

(Measurement Conditions)
Column: Shim-pack GPC-803C+GPC-805C (serially-connected)
Column temperature: 45° C.
Eluting solution: Chloroform
Detector: RID (differential refraction detector)
Sample concentration: 2.5 g/L (dissolved in chloroform)

TABLE 1

| Irradiation dose | Sample | Mw/Mn | Mw average | Decreasing rate |
|---|---|---|---|---|
| 0 kGy | Sample 1 | 1.57 | 82114 | 63% |
| 0 kGy | Sample 2 | 1.43 | 78046 | 87% |
| 0 kGy | Sample 3 | 1.51 | 103815 | 80% |
| 40 kGy | Sample 1 | 1.55 | 61370 | 75% |
| 40 kGy | Sample 2 | 1.53 | 57099 | 73% |
| 40 kGy | Sample 3 | 1.60 | 70503 | 68% |

TABLE 2

| | Irradiation dose (kGy) | Weight average molecular weight (MW) | Decreasing rate (%) |
|---|---|---|---|
| Electron-beam irradiation | 0 (Unirradiated) | 73034 | — |
| | 10 | 63181 | 86.5 |
| | 20 | 68165 | 93.3 |
| | 40 | 59382 | 81.3 |
| Gamma-ray irradiation | 0 (Unirradiated) | 77798 | — |
| | 5 | 67777 | 87.1 |
| | 10 | 70657 | 90.8 |
| | 25 | 58221 | 74.8 |
| | 50 | 53046 | 68.2 |
| | 100 | 37747 | 48.5 |

Example 2

With the use of a microneedle base (weight average molecular weight: 37,747) which was irradiated with a 100 kGy gamma ray, a strength test of microneedles made from polylactic acid by use of an excised human skin was performed. The strength test was performed as follows: an excised human skin was adjusted to have a thickness of about 700 um by an electric dermatome, and fixed on a cork board; and subsequently, a microneedle base was set on the skin and pressed from its back by a finger for 5 seconds at 3 kgf/patch. As a result of the strength test, no breaking of the base itself was observed, and breaking and bending of tip parts of only microneedles provided at an outermost periphery were observed. In view of this, it was demonstrated that even the polylactic acid microneedle device with a weight average molecular weight of about 40,000 was sufficient in terms of base strength and needle strength.

Example 3

Figure 2:
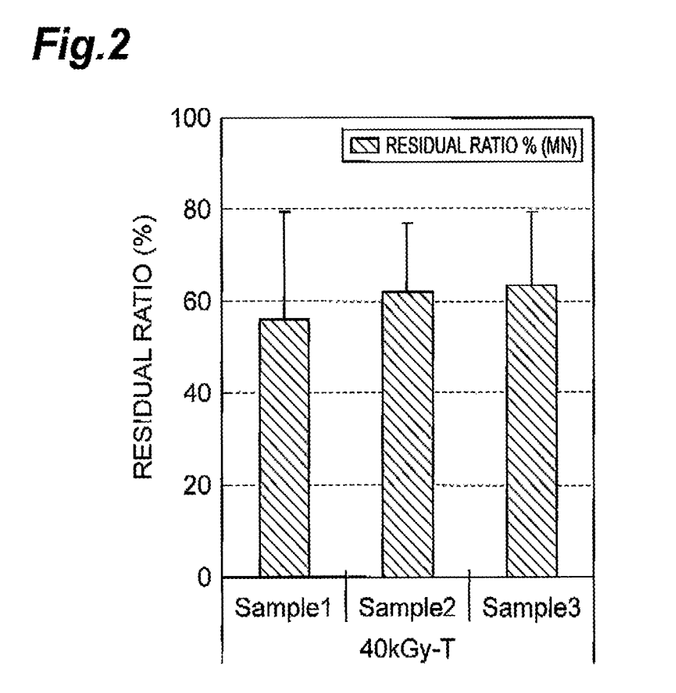
FIG. 2 relates to Example 3 and is a graph showing a result obtained by measuring, by a GM measuring device, a content of a drug remaining on a microneedle base after piercing excised human skin with a coated microneedle device by finger pressing for 5 seconds.

In Example 3, a delivery test (an excised-human-skin piercing test) of a drug was performed with the use of an excised human skin and in the same group configurations as the breaking strength test of the microneedle base. As the drug, radiolabeled $^{14}$C-OVA and Cold OVA were used to prepare a mixed liquid with pullulan. A composition of a coating liquid was assumed (30% pullulan/20% OVA), and coating was performed on tip parts of needles so that the coating had a height of 100 um. A specific method of the coating was such that coating was performed on microneedles by use of a metal mask (standard: one side of an aperture is 220 um, a thickness is 100 um, and humidity is 85% or more at room temperature), thereby forming a microneedle device. Subsequently, after piercing an excised human skin with the microneedles thus coated by finger pressing (3 kg/patch) for 5 seconds, a content of the drug remaining on the microneedle base was measured by a GM measuring device (n=3). As shown in results in FIG. 2, every group shows a residual ratio at the same level, and thus, it was found that the performance of the microneedle was maintained.

Example 4

Figure 3:
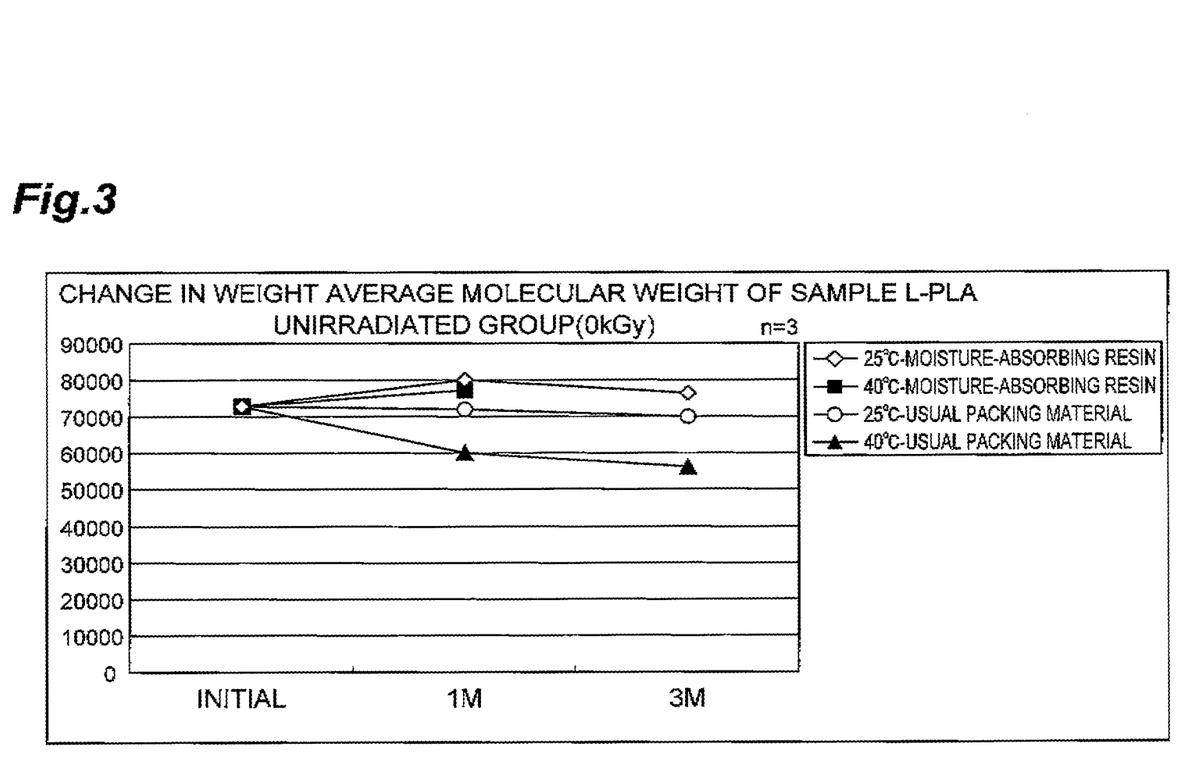
FIG. 3 relates to Example 4 and is a graph showing a result obtained by measuring a decrease in a weight average molecular weight of polylactic acid by use of samples (electron-beam unirradiated products) of a microneedle molded using a poly-L-lactic acid resin.
Figure 4:
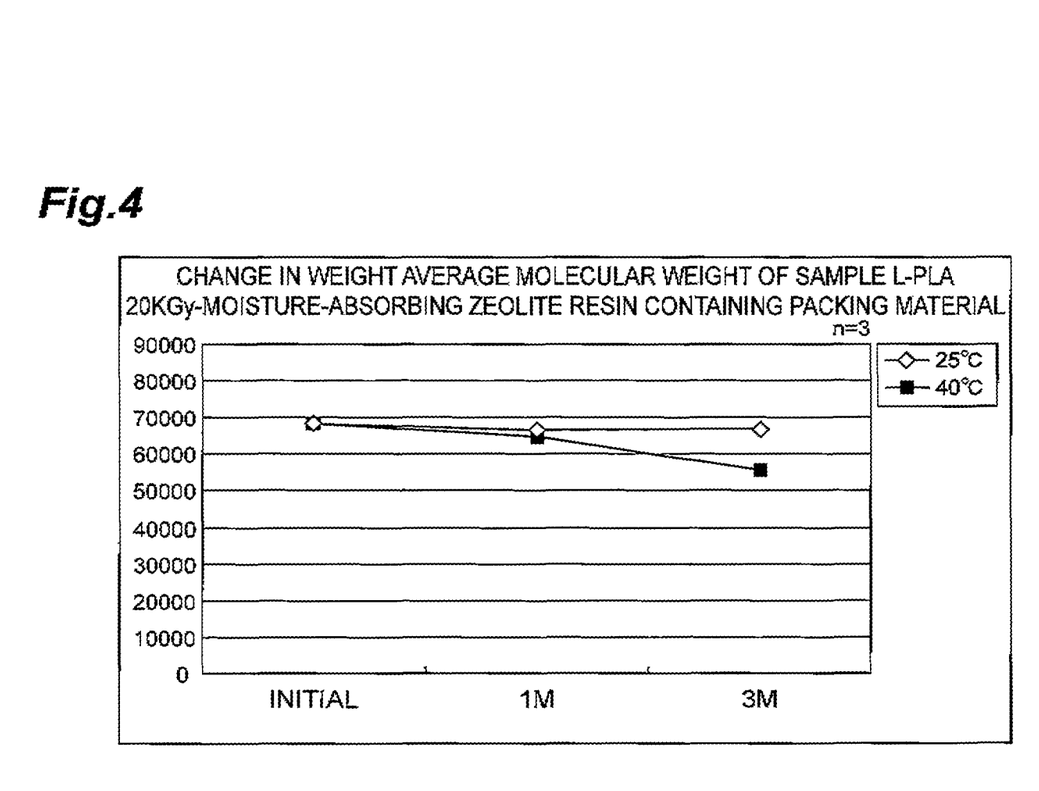
FIG. 4 relates to Example 4 and is a graph showing a result obtained by measuring a decrease in a weight average molecular weight of polylactic acid in a case where samples of a microneedle molded using a poly-L-lactic acid resin are irradiated with an electron beam (20 kGy) and the resultant products are heat-sealed with moisture-catch packing materials and then stored.
Figure 5:
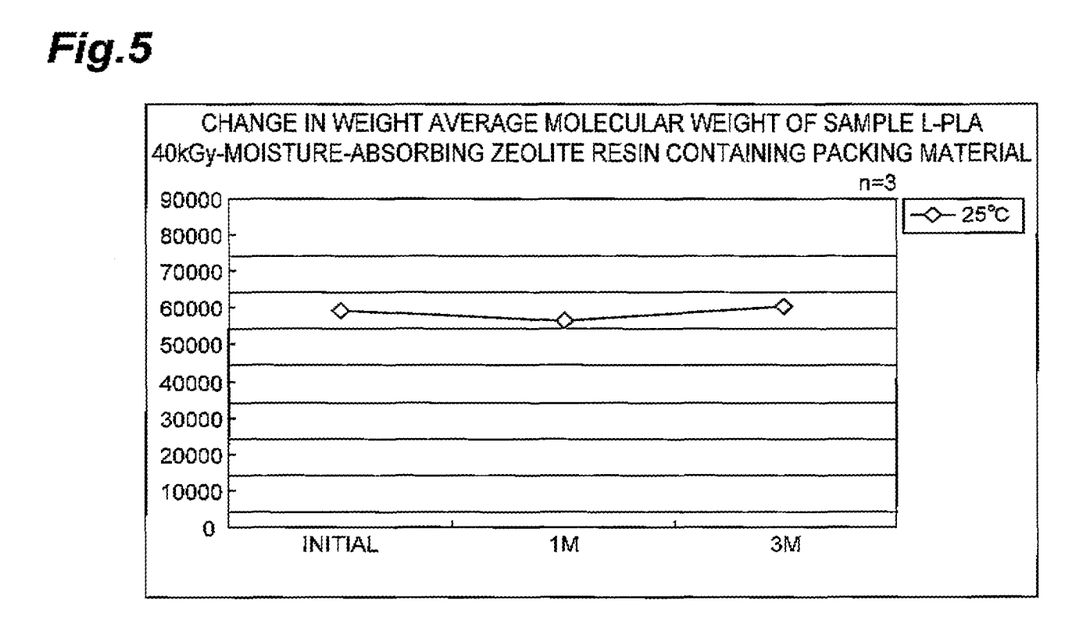
FIG. 5 relates to Example 4 and is a graph showing a result obtained by measuring a decrease in a weight average molecular weight of polylactic acid in a case where samples of a microneedle molded using a poly-L-lactic acid resin are irradiated with an electron beam (40 kGy) and the resultant products are heat-sealed with moisture-catch packing materials and then stored.
Figure 6:
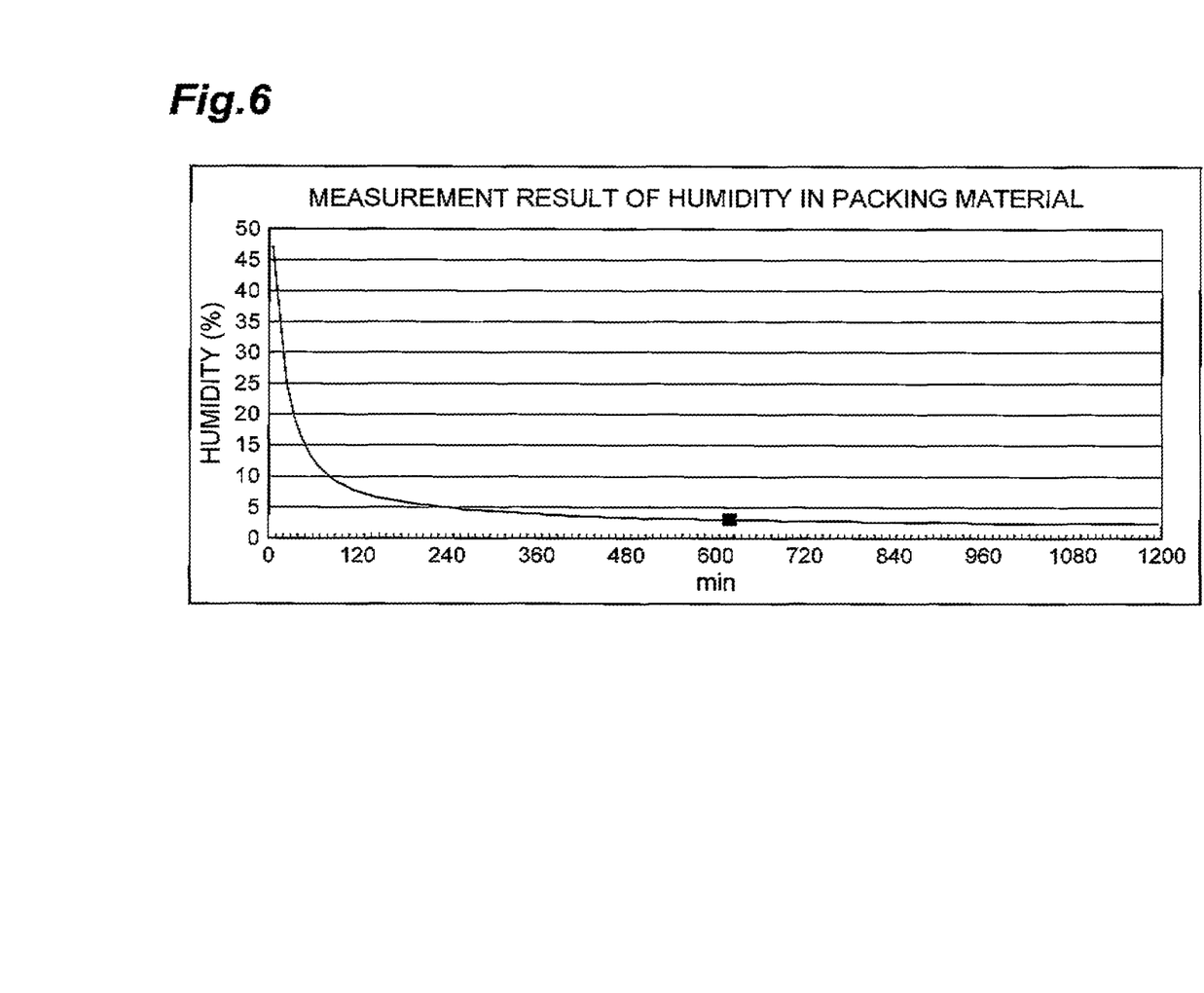
FIG. 6 relates to Example 4 and is a graph showing changes in humidity in a packing material.

In Example 4, a test was performed to measure a decrease in the weight average molecular weight of polylactic acid due to storage. A stability evaluation of the resin was performed by use of samples of electron-beam unirradiated products (weight average molecular weight after molding: about 70,000) of microneedles molded by using a poly-L-lactic acid resin, and samples of electron-beam irradiated products (40 kGy) thereof. For an index of the stability, the weight average molecular weight was used, and it was measured by the aforementioned GPC method. As a storage form, heat sealing was performed by use of two types of packing materials, i.e., a usual aluminum packing material and a high-performance aluminum packing material to which a moisture-absorbing function was given by a moisture-absorbing zeolite resin. Storage conditions were such that samples were stored in constant-temperature baths of 25° C. and 40° C. for 3 months, and they were taken out therefrom at some points of time to measure the weight average molecular weights thereof. As apparent from FIG. 3, it was demonstrated that microneedle samples which were stored in usual packing materials exhibited a decrease in the weight average molecular weight over time, and that the tendency thereof was temperature-dependent. On the other hand, samples (moisture group) stored in high-performance packing materials to which the moisture-absorbing function was given exhibited almost no decrease in the weight average molecular weight and the values thereof were constant. Similar tendencies were shown about microneedle samples which were irradiated with an electron beam (see FIG. 4 and FIG. 5), and although a little decrease tendency was observed in a sample stored at 40° C., almost no change was observed in a sample stored at 20° C., Note that when the humidity in a packing material with a dry function used in this test was measured, it was shown that the humidity decreased to a relative humidity of about 3% for about 10 hours, and even after that, a low humidity was stably maintained (see FIG. 6).

Example 5

A composition of a carrier (coating agent) made from model physiologically active ingredients (octreotide acetate) and propylene glycol or glycerin, and a relation between viscosity and content of physiologically active ingredients in the carrier
<Setting Conditions>
(a) Microneedle
    Material: Polylactic acid having a weight average molecular weight of about 80,000, Height: 500 μm, Density: 625 needles/cm$^2$, Formulation area of a microneedle base: 1 cm$^2$/patch
(b) Metal Mask Plate
    Pitch: 400 μm, Mask thickness: 100 μm, Opening: square shape (one side: 250 μm)
(c) Environmental Setting: Room Temperature (25° C.)
    <Viscosity Measurement>
The concentration of octreotide acetate and the concentration of propylene glycol or glycerin were set as shown in Table 3 and Table 4, and the materials were set in a rotating/revolving mixer to prepare a carrier (a coating agent). The viscosity of the obtained carrier (the coating agent) was measured 10 times by use of a micron-sample viscometer (RHEOSENSE INC., Micron Sample-Viscometer/Rheometer-on-a-chip VROCTM); calculated average values are shown in. Table 3 and Table 4.
    <Measurement of Content of Octreotide Acetate in Carrier (Coating Agent)>
The concentration of octreotide acetate and the concentration of propylene glycol or glycerin were set as shown in Table 3 and Table 4, and the materials were set in a rotating/revolving mixer to prepare a carrier (a coating agent). Application of the carrier (the coating agent) to microneedles was performed by a predetermined method. More specifically, the carrier the coating agent) was swept by a spatula to fill openings of a metal mask with the carrier. Microneedles (needles) were inserted in the openings thus filled, and then taken out therefrom, and subsequently, the carrier (the coating agent) thus applied on the microneedles was extracted by purified water. By a BCA method (an octreotide standard), the content (an amount deposited) of octreotide acetate per one patch (sheet) of a microneedle device was measured 10 times; calculated average values are shown in Table 3 and Table 4.

TABLE 3

| Octreotide acetate (% by weight) | Propylene glycol (% by weight) | Viscosity Avg. (cps) | Content Avg. (μg/patch) |
|---|---|---|---|
| 20 | 80 | 200 | 4 |
| 40 | 60 | 1600 | 36 |
| 50 | 50 | 5400 | 121 |
| 60 | 40 | 15000 | 243 |
| 70 | 30 | 45000 | 237 |
| 80 | 20 | 133000 | 97 |

TABLE 4

| Octreotide acetate (% by weight) | Glycerin (% by weight) | Viscosity Avg. (cps) | Content Avg. (μg/patch) |
|---|---|---|---|
| 20 | 80 | 2900 | 6 |
| 30 | 70 | 9000 | 39 |
| 35 | 65 | 12000 | 53 |
| 40 | 60 | 15000 | 89 |
| 50 | 50 | 21000 | 169 |
| 60 | 40 | 27000 | 149 |

As shown in Table 3 and Table 4, it was found that the viscosity of the carrier (the coating agent) increases as the content of octreotide acetate (physiologically active ingredients) in the carrier (the coating agent) increases, and that the content of octreotide acetate in the carrier (the coating agent) increases as the viscosity increases to a certain viscosity, but the content shifts to a decrease after the viscosity exceeds the certain viscosity.

As to propylene glycol in Table 3, since the content of octreotide acetate shifts to a decrease between a viscosity of 15000 cps and a viscosity of 45000 cps, the most suitable viscosity is from 200 cps to 45000 cps, and a viscosity of more than that value is unfavorable from the viewpoint of administration efficiency.

As to glycerin in Table 4, since the content of octreotide acetate shifts to a decrease between a viscosity of 21000 cps and a viscosity of 27000 cps, the most suitable viscosity is from 2000 cps to 25000 cps, and a viscosity of more than that value is unfavorable from the viewpoint of administration efficiency.

As such, it was suggested that application of a carrier (a coating agent) made from predetermined materials to microneedles having a predetermined strength or more attained more preferable administration efficiency.

Example 6

In Example 6, in order to evaluate a relation between height of a coating to coat microneedles and migration of a drug (physiologically active ingredients) into skin, microneedle devices (material of microneedles: L-polylactic acid having a weight average molecular weight of about 80,000, needle height: 480 μM, needle shape: square pyramid, needle density: 625 needles/cm$^2$, composition of coating: 20% OVA (ovalbumin)/20% pullulan/$^{14}$C-OVA) having different heights of the coating were produced as Reference Examples 1 to 5, and drug migration into the skin was calculated (see Table 5). Note that the height of the coating as used herein refers to a distance from a tip of a needle, as an origin, to a lowest-limit position of the needle to which a coating liquid is distributed.

The application of the microneedle device and the calculation of the drug migration were performed as follows. That is, after microneedles were brought into contact with a skin (excised hairless rat skin), an applicator to give an impact of 0.4 J on a device was used for piercing the skin with the needles, and 3 minutes later, the microneedle device was removed. Subsequently, an amount of OVA which migrated to the skin was calculated by measuring $^{14}$C-OVA remaining on the microneedles.

As a result of the calculation, it was found that in cases where the height of the coating exceeds a certain height, no matter how much the amount of the coating is increased, the migration of the drug (physiologically active ingredients) to the skin tends not to change. That is, it was suggested that a drug can be administered more efficiently if the height of the coating is 100 to 200 μm.

TABLE 5

| | Height of coating | Amount of coating | Migration to skin (migration rate) |
|---|---|---|---|
| Reference example 1 | 140-160 μm | 34.3 μg | 34.2 μg (91.0%) |
| Reference example 2 | 180-220 μm | 59.3 μg | 30.7 μg (51.8%) |
| Reference example 3 | 220-240 μm | 91.2 μg | 40.6 μg (44.5%) |
| Reference example 4 | 140-160 μm | 106.8 μg | 65.3 μg (61.1%) |
| Reference example 5 | 180-220 μm | 97.1 mg | 28.6 μg (29.5%) |

Industrial Applicability

According to the present invention, a microneedle made from polylactic acid maintains its performance even after electron-beam irradiation sterilization, and the performance can be maintained for a long time by storing it while humidity is managed. This allows the utilization of a microneedle device to be markedly increased, and thus the present invention has an industrial applicability.

Reference Signs List

1 . . . microneedle device, 2 . . . microneedle array, 3 . . . microneedle, and 7 . . . coating.

The invention claimed is:

1. A microneedle device comprising a microneedle array provided with microneedles made from polylactic acid having a weight average molecular weight of 40,000 or more, wherein at least a part of the microneedle array is coated with a carrier containing a physiologically active ingredient and the viscosity of the carrier is 100 cps to 100000 cps; and wherein the weight average molecular weight is a weight average molecular weight after sterilization by electron-beam or gamma-ray irradiation.

2. The microneedle device according to claim 1, wherein the carrier is pullulan, propylene glycol, glycerin, or a carboxyvinyl polymer.

3. The microneedle device according to claim 1, wherein the viscosity of the carrier is 500 cps to 60000 cps.

4. The microneedle device according to claim 1, wherein a height of the coating is a distance from a tip to a lowest-limit position of the needle to which a coating liquid is distributed, and the height of the coating is 100 μm to 200 μm.

5. The microneedle device according to claim 2, wherein the carrier is propylene glycol.

6. The microneedle device according to claim 2, wherein the carrier is glycerin.

7. The microneedle device according to claim 2, wherein the carrier is a carboxyvinyl polymer.

* * * * *

UNITED STATES PATENT AND TRADEMARK OFFICE
CERTIFICATE OF CORRECTION

| | | |
|---|---|---|
| PATENT NO. | : 8,747,362 B2 | Page 1 of 1 |
| APPLICATION NO. | : 13/376656 | |
| DATED | : June 10, 2014 | |
| INVENTOR(S) | : Terahara et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 0 days.

Signed and Sealed this
Fourth Day of August, 2015

Michelle K. Lee
*Director of the United States Patent and Trademark Office*